(12) United States Patent
Zhang (10) Patent No.: US 10,406,239 B2
(45) Date of Patent: Sep. 10, 2019

(54) WATER-SOLUBLE DOCETAXEL ANTICANCER DRUG COMPOUND AND PREPARATION METHOD AND USE THEREOF

(71) Applicant: NANJING YOUYI MEDICAL TECHNOLOGY CO., LTD, Nanjing, Jiangsu (CN)

(72) Inventor: Yuehua Zhang, Jiangsu (CN)

(73) Assignee: NANJING YOUYI MEDICAL TECHNOLOGY CO., LTD, Nanjing, Jiangsu (CN)

( * ) Notice: Subject to any disclaimer, the term of this patent is extended or adjusted under 35 U.S.C. 154(b) by 0 days.

(21) Appl. No.: 15/762,985

(22) PCT Filed: Jan. 22, 2016

(86) PCT No.: PCT/CN2016/071696
§ 371 (c)(1),
(2) Date: Mar. 23, 2018

(87) PCT Pub. No.: WO2017/049821
PCT Pub. Date: Mar. 30, 2017

(65) Prior Publication Data
US 2018/0303949 A1    Oct. 25, 2018

(30) Foreign Application Priority Data

Sep. 26, 2015 (CN) .......................... 2015 1 0624350

(51) Int. Cl.
| | | |
|---|---|---|
| *C07D 305/14* | (2006.01) | |
| *A61K 9/08* | (2006.01) | |
| *A61K 31/337* | (2006.01) | |
| *A61K 31/765* | (2006.01) | |
| *C08G 65/48* | (2006.01) | |
| *A61K 47/60* | (2017.01) | |
| *A61K 9/00* | (2006.01) | |

(Continued)

(52) U.S. Cl.
CPC ............ *A61K 47/60* (2017.08); *A61K 9/0019* (2013.01); *A61K 9/08* (2013.01); *A61K 9/107* (2013.01); *A61K 31/337* (2013.01); *A61K 31/765* (2013.01); *A61K 47/02* (2013.01); *A61K 47/26* (2013.01); *A61P 35/00* (2018.01); *C07D 305/14* (2013.01); *C08G 65/332* (2013.01); *C08G 65/48* (2013.01)

(58) Field of Classification Search
CPC ...... C07D 305/14; A61K 9/08; A61K 31/337; A61K 31/765; C08G 65/48
See application file for complete search history.

(56) References Cited

U.S. PATENT DOCUMENTS 5,824,701 A     10/1998 Greenwald et al.
2010/0010194 A1*  1/2010 Zhang .............. C08G 65/33344
                                              530/345

FOREIGN PATENT DOCUMENTS

CN     101486744        7/2009
CN     102731442 A     10/2012
(Continued)

OTHER PUBLICATIONS

Du, Wenting et al., "Research Progress of Water Soluble Derivatives of Taxol", Chinese Journal of Modern Applied Pharmacy, vol. 22, No. 1, Feb. 28, 2005, pp. 29-31, an English Abstract provided.
Greenwald, R.B. et al., "Highly Water Soluble Taxol Derivatives: 2'-Polyethyleneglycol Esters as Potential Prodrugs", Bioorganic & Medicinal Chemistry Letters, vol. 4, No. 20, Oct. 20, 1994, pp. 2465-2470.

*Primary Examiner* — Laura L Stockton
(74) *Attorney, Agent, or Firm* — Novick, Kim & Lee, PLLC; Allen Xue (57) ABSTRACT

The present invention discloses a water-soluble docetaxel anticancer drug compound having the structure of Formula I below:

I in which R=—$CH_3$, —$CH_2CH_3$, —$CH_2CH_2CH_3$, or —$CH_2CH_2CH_2CH_3$; and n=5-500.
The active moiety docetaxel in the anticancer drug compound is covalently conjugated to a polyethylene glycol monoalkyl ether through a linker diglycoloyl (carbonyl methoxyacetyl) to form the water-soluble docetaxel anticancer drug compound.
The present invention also relates to a preparation method of the drug compound and use thereof.

13 Claims, 5 Drawing Sheets

(51) Int. Cl.
  *A61K 47/02* (2006.01)
  *A61K 47/26* (2006.01)
  *A61K 9/107* (2006.01)
  *C08G 65/332* (2006.01)
  *A61P 35/00* (2006.01)

(56) References Cited

FOREIGN PATENT DOCUMENTS

| | | |
|---|---|---|
| CN | 103641925 A | 3/2014 |
| WO | 9511020 A1 | 4/1995 |

* cited by examiner

WATER-SOLUBLE DOCETAXEL ANTICANCER DRUG COMPOUND AND PREPARATION METHOD AND USE THEREOF

BACKGROUND

Technical Field

The present invention relates to a novel anticancer drug compound and preparation method and use thereof, and in particular to a water-soluble docetaxel anticancer drug compound, preparation method and use thereof as an anticancer drug.

Background of the Invention

A barrier is encountered in the drug development of many compounds having anticancer activity due to their insolubility or poor stability in water and/or other biocompatible solvents, which often leads to delayed drug development. It is estimated that as high as 40% of the screened candidate drug compounds having potential medicinal value are denied for entering the formulation research and development phase because of their poor water solubility, and about 30% of existing drugs are poorly soluble. There are several technologies currently under study and development to address the problem of poor soluble drug compounds, including solubility enhancing complexing technology, nanoparticle technology, microemulsion technology, solubility enhancing formulation technology, liposome formulation technology, fat-soluble and water-soluble prodrug technology, as well as new polymer drug delivery technology.

Docetaxel (Formula 1), also known as taxotere, is a lipophilic taxane anticancer drug belonging to cytostatics, which achieves an anti-tumor effect by destroying the mitosis of tumor cells by enhancing the tubulin polymerization and inhibiting the tubulin depolymerization to form a stable non-functional microtubule. Docetaxel has an intracellular concentration that is 3 times higher than that of paclitaxel and also a longer intracellular residence time, and thus has a more potent anti-tumor activity than paclitaxel. In clinic, docetaxel is mainly used for the treatment of advanced breast cancer, ovarian cancer, non-small cell lung cancer, head and neck cancer, and small cell lung cancer; and also has a certain effect on gastric cancer, pancreatic cancer, and melanoma.

Formula 1

Molecular structure of docetaxel

Docetaxel has high anti-tumor activity, good safety and tolerability, and has been widely used clinically since it became available. However, similar to other anti-tumor drugs, docetaxel cannot selectively recognize tumor cells from normal cells, so the side effects are also particularly prominent. There are more and more reports about its adverse reactions. The main adverse reactions found at present include fluid retention, skin toxicity such as systemic erythema, pruritus and rash, severe weakness and paralysis; hematologic toxicity including leucopenia, neutropenia and febrile neutropenia; non-hematologic toxicities including alopecia, sensory and motor neurotoxicity, stomatitis, weakness nausea, vomiting, diarrhea, and other reactions of the digestive system.

In order to reduce the toxic side effects of docetaxel and broaden the scope of its clinical application thereof, many efforts have been made by scientists in China and other countries to develop new formulations of docetaxel. Docetaxel is insoluble in water, leading to a low drug loading of formulation in clinic, which limits the dose and impacts the clinical efficacy; and the oral bioavailability is poor, being less than 8%. At present, docetaxel is marketed as a docetaxel injection. In this formulation, Tween 80 is used as a solvent, which has toxic side effects. Moreover, docetaxel is prone to degradation in aqueous solutions and thus difficult to be stored.

In order to solve the above drawbacks of docetaxel, scientists have put many efforts to develop new drug delivery systems, for example, (1) liposome formulations, for example, docetaxel loaded nanoliposome prepared by film dispersion-ultrasonication, which can achieve the purpose of small particle size, high drug encapsulation rate and controlled release; (2) long-circulating formulations, prepared by loading docetaxel on a carrier modified with a hydrophilic polyethylene glycol, which can escape the in vivo phagocytosis of the reticulo-endothelial system in liver and spleen, thereby extending the blood circulation time; (3) injectable docetaxel microemulsions prepared by using soybean oil and triacylglycerol as an oil phase and Poloxamer 188 and soybean phospholipids as an emulsifier, where the microemulsions have high stability and increased drug load while the particle size and the drug encapsulation rate are not affected; (4) micelle formulations, in which the commonly used docetaxel-loaded micellar carriers include polyethylene glycol-polylactic acid block copolymers, polyvinylpyrrolidone-poly-D,L (racemic) lactic acid block copolymers, as well as pH sensitive block copolymer micelles and heat-sensitive polymer micelles; (5) active targeting nano-drug delivery systems of docetaxel. Great progress has been made in studies on these new formulations in terms of increasing the water solubility of docetaxel, reducing the toxic side effects, and enhancing the bioavailability of the drug. This not only provides a potential route to increase the water solubility of docetaxel, reduce the toxic side effects, and enhance the bioavailability of the drug, but also provides cancer patients with the hope of safe medication. However, these drug delivery systems suffer from more or less defects, such as low encapsulation rate, drug leakage, and stability-related and other problems that need to be further resolved.

BRIEF DESCRIPTION OF THE INVENTION

An object of the present invention is to provide a novel water-soluble docetaxel anticancer drug compound having high anti-cancer activity and low toxicity. The new compound can not only be dissolved in water, but also form nano-particles in the aqueous solution, and has the function of sustained-release of drug.

Another object of the present invention is to provide a method for synthesizing the water-soluble docetaxel anticancer drug compound.

Another object of the present invention is to provide a composition comprising the water-soluble docetaxel anticancer drug compound, which is an injection prepared by dissolving the water-soluble docetaxel anticancer drug compound as a prodrug directly in water, saline or a glucose solution.

Also, another object of the present invention is to provide use of the compound in the preparation of anti-cancer drugs.

The water-soluble docetaxel anticancer drug compound of the present invention comprises of a lipophilic anti-cancer drug active moiety and a hydrophilic moiety. The lipophilic anti-cancer drug active moiety is a molecule of the drug compound docetaxel having anticancer activity, and the hydrophilic moiety is a water-soluble alkoxy polyethylene glycol. The alkoxy polyethylene glycol is covalently conjugated to the anti-cancer drug compound docetaxel by a linker diglycoloyl (oxydiacetyl, or diglycolyl) through an ester linkage, to form the anti-cancer drug compound of the present invention.

To achieve the objects of the present invention, the following technical solutions are adopted. A water-soluble docetaxel anticancer drug compound is provided. The new drug compound has the structure of general Formula I below:

I in which R is C1-C5 alkyl, and generally and preferably the following groups:

a) methyl (—CH$_3$);
b) ethyl (—CH$_2$CH$_3$);
c) propyl (—CH$_2$CH$_2$CH$_3$); and
d) butyl (—CH$_2$CH$_2$CH$_2$CH$_3$), and
the degree of polymerization n=5-500.

The present invention further relates to a method for preparing the water-soluble docetaxel anticancer drug compound, which comprises of the following steps:

1) A polyethylene glycol monoalkyl ether (1) reacts with diglycolic acid or diglycolic anhydride to produce a polyethylene glycol monoalkyl ether diglycolate (2); and

2) The polyethylene glycol monoalkyl ether diglycolate (2) or an acyl chlorinated product (3) of the polyethylene glycol monoalkyl ether diglycolate obtained in Step 1) reacts with docetaxel to produce the water-soluble docetaxel anticancer drug compound (I).

Specifically, the method comprises of the following steps:

1) The polyethylene glycol monoalkyl ether (1) reacts with diglycolic anhydride in the presence of tin (II) 2-ethylhexanoate, aluminum trichloride or cesium carbonate as a catalyst to produce the polyethylene glycol monoalkyl ether diglycolate (2); or the polyethylene glycol monoalkyl ether (1) reacts with excess diglycolic acid in the presence of 4-dimethylaminopyridine (DMAP) and 2-chloro-1-methylpyridinium iodide (CMPI), or N,N'-dicyclohexylcarbodiimide (DCC) and 4-dimethylaminopyridine (DMAP) as a catalyst, to produce the polyethylene glycol monoalkyl ether diglycolate (2);

2) The polyethylene glycol monoalkyl ether diglycolate (2) reacts with an acyl chlorinating agent (e.g. thionyl chloride) to produce the acyl chlorinated product (3); and 3) The acyl chlorinated product (3) obtained in Step 2) reacts with docetaxel in the presence of a base (e.g. triethyl amine, pyridine, 4-dimethylaminopyridine, sodium carbonate, potassium carbonate, or cesium carbonate) as a catalyst to produce the water-soluble docetaxel anticancer drug compound (I); or the polyethylene glycol monoalkyl ether diglycolate (2) obtained in Step 1) reacts with docetaxel in the presence of 4-dimethylaminopyridine (DMAP) and 2-chloro-1-methylpyridinium iodide (CMPI) or N,N'-dicyclohexylcarbodiimide (DCC) and 4-dimethylaminopyridine (DMAP) as a catalyst to produce the water-soluble docetaxel anticancer drug compound (I).

The present invention also relates to a formulation of the water-soluble docetaxel anti-cancer drug. Such a novel water-soluble docetaxel anticancer drug compound can be directly dissolved in water, saline (0.9% sodium chloride) or glucose (5%) for injection to prepare an injection that is a micelle formulation.

The following technical solution is adopted. An injection of the water-soluble docetaxel anticancer drug compound comprises of 1) a water-soluble docetaxel anticancer drug compound having the structure of Formula I; and 2) water, saline (0.9% sodium chloride) or a glucose solution (5%) for injection.

In the injection, the content of the water-soluble docetaxel drug compound in the formulation may be about 0.005% to 5.0%, preferably about 0.01% to 2.5%, and more preferably about 0.1% to 2.0%.

The drug compound has good water solubility and forms nanoparticle micelles in the aqueous solution. The compound comprises of a lipophilic anticancer drug active moiety and a hydrophilic polyethylene glycol moiety. The entire molecule is not only a drug molecule, but also a surfactant, with which nanomicelles can be automatically formed after being dissolved in water without adding any surfactant or other aid. As a solvent-based drug delivery system, the nanoparticle micelles also have the function of sustained-release of drug.

The drug compound of the present invention has high anticancer activity, low toxicity, and good water solubility. As a prodrug, the drug compound can be hydrolyzed or enzymatically hydrolyzed to release the active drug molecule docetaxel in an aqueous solution or in the body fluid. The applicant had tried different linkers such as carbonyl —(C=O)—, C1-10 alkylenecarbonyl (—(CH$_2$)$_n$CO—), C1-10 bisacyl (—(C=O)(CH$_2$)$_n$(C=O)—, such as glutaryl), and —P(=O)(R)—, etc., with which, however, no satisfactory results are achieved in terms of the antitumor activity and the drug delivery systems.

The present invention also provides use of the novel drug compound, namely the water-soluble docetaxel anticancer drug compound according to the present invention in the preparations of anticancer drugs.

For example, the drug compound of the present invention is useful in the preparation of a medicament for treating cancer. The drug compound of the present invention is useful in the treatment of cancers including hematological cancers such as leukemia, lymphoma and myeloma; and non-hematological cancers such as solid tumor (e.g. breast cancer, ovarian cancer, pancreatic cancer, colon cancer, rectal cancer, non-small cell lung cancer, and bladder cancer), sarcoma and glioma.

The efficacy and toxicity of the drug compound of the present invention are determined by in vitro cell or in vivo animal experiments, such as ED50 (50% effective dose or median effective dose: a dose at which 50% of the subjects have a positive reaction occurs), LD50 (50% lethal dose or median lethal dose: a dose at which 50% of the subjects are killed) and GI50 (concentration of the anti-cancer drug that inhibits the growth of cancer cells by 50%). The ratio of the median lethal dose (LD50)/the half effective dose (ED50) is often referred to as the therapeutic index to indicate the safety of the drug. Drugs with a large therapeutic index are safer than drugs with a low therapeutic index.

The novel anticancer drug compound of the present invention aims to increase the therapeutic index and the safety as well as the therapeutic effect of the drug. The dosage range for use in human can be determined from the dosages of the drug obtained from in vitro cell experiments and in vivo animal experiments. The dosage of this compound is preferably in a range around ED50 with little or no toxicity. Generally, the dosage varies depending on the dosage form employed, the patient's sensitivity, and the route of administration. Reference may be made to the conventional dosage of a same or similar drug such as Taxotere®, and Docetaxel injection, etc.

The drug compound of the present invention may be used alone or in combination with one or more other therapeutic agents. For example, the drug compound of the present invention may be used with the following therapeutic agents in the treatment of cancer, including but not limited to: androgen Inhibitors, for example, flutamide and luprolide; anti-estrogen agent, for example, tomoxifen; antimetabolites and cytotoxic drugs, for example, daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idamycin; hormone, for example medroxyprogesterone, ethinyl estradiol, estradiol, leuprolide, megestrol, octreotide, diethylstilbestrol, chlorotrianisene, etoposide, podophyllotoxin and goserelin; nitrogen mustard derivatives, for example, melphalan, chlorambucil and thiotepa; steroids, for example, betamethasone; and other anti-tumor drugs, for example, live *mycobacterium bovis*, dicarbazine, asparaginase, leucovorin, mitotane, vincristine, and vinblastine etc.

In the present invention, a molecule of the drug compound docetaxel having anticancer activity is covalently conjugated to a water-soluble alkoxy polyethylene glycol through diglycoloyl to obtain a water-soluble docetaxel anticancer drug compound. The compound comprises of a lipophilic anti-cancer drug active moiety and a hydrophilic polyethylene glycol moiety, such that the drug molecule has the dual functions of a drug and a surfactant, and can be dissolved in water, saline or a glucose solution for injection in the absence of a surfactant, to form nanoparticle micelles, which is directly prepared into an injection. The novel anticancer drug compound of the present invention has both high anticancer activity and good water solubility, can improve the duration of action (half-life) and the therapeutic effect of docetaxel in vivo under physiological conditions, and has the action of sustained release, as well as reduced toxic side effects. The drug compound can be prepared into injections, and widely used in the treatment of hematological and non-hematological cancers, thus providing a new method and approach for the clinical use of docetaxel.

The present invention will be described in detail below with reference to specific embodiments. However, the protection scope of the present invention is not limited thereto, but as limited by the appended claims.

DETAILED DESCRIPTION OF THE INVENTION

The following examples are provided for illustrating the synthesis, preparation, in vitro cell experiments and in vivo pharmacodynamics of the water-soluble docetaxel anticancer drug compound of the present invention. In these examples, detailed descriptions are given with polyethylene glycol monomethyl ether docetaxel-2'-diglycolate as an example. The water-soluble docetaxel anticancer drug compounds within the scope of the present invention are synthesized by using the same or similar synthesis method, which are verified to have the same or similar results. The examples described facilitate the understanding and implementation of the present invention and do not constitute limitations on the present invention.

Example 1. Synthesis of Polyethylene Glycol Monomethyl Ether (Mn=1000) Docetaxel-2'-Diglycolate

The water-soluble docetaxel anticancer drug compound was synthesized through a process comprising of the following steps.

1) Synthesis of Polyethylene Glycol Monomethyl Ether (Mn=1000) Diglycolate

Method 1:

The reaction scheme was as shown below:

Experimental Steps:

To a 100 mL round-bottom flask, 2.400 g (2.4 mmol) of dried polyethylene glycol monomethyl ether (Mn=1000), 0.557 g (4 mmol) of diglycolic anhydride, and 200 mg of tin (II) 2-ethylhexanoate were added, followed by 30 mL of xylene. The mixture was stirred and heated to reflux under nitrogen atmosphere until the reaction was complete. The xylene was removed from the reaction solution by rotary evaporation. 20 mL of ethyl acetate was added and stirred. 10 mL of diethyl ether was then added, and a white solid was precipitated out. The solid was filtered off, and the filtrate was concentrated to 10 mL by rotary evaporation. After separation by column chromatography (on 100-200 mesh silica gel as a stationary phase, eluting with a mixture of acetonitrile and 1,4-dioxane), 1.865 g of polyethylene glycol monomethyl ether (Mn=1000) diglycolate was obtained (yield 69.3%).

Method 2: To a 100 mL round-bottom flask, 0.644 g (4.8 mmol) of diglycolic acid, 1.450 g (12 mmol) of 4-dimethylaminopyridine, 1.530 g (6 mmol) of 2-chloro-1-methylpyridinium iodide, and 30 mL of N,N-dimethyl acetamide were added and electromagnetically stirred. A solution of 2.400 g (2.4 mmol) of dried polyethylene glycol monomethyl ether (Mn=1000) and 30 mL of N,N-dimethyl acetamide was slowly added dropwise to the reaction solution. The reaction was continued for 12 hrs at room temperature under nitrogen atmosphere. The filtrate was concentrated to 10 mL by rotary evaporation. After separation by column chromatography (on 100-200 mesh silica gel as a stationary phase, eluting with a mixture of acetonitrile and 1,4-dioxane), 1.631 g of polyethylene glycol monomethyl ether (Mn=1000) diglycolate was obtained (yield 60.6%).

2) Synthesis of Polyethylene Glycol Monomethyl Ether (Mn=1000) Docetaxel-2'-Diglycolate (XBB-023)

The reaction scheme was as shown below:

-continued

I 1.667 g (1.49 mmol) of polyethylene glycol monomethyl ether (Mn=1000) diglycolate was dissolved in 30 mL of anhydrous toluene in a 100 mL round-bottom flask. 550 μL (7.45 mmol) of thionyl chloride and 2 drops of DMF were added, electromagnetically stirred, and reacted for 4 h at room temperature under nitrogen atmosphere. Toluene and excess thionyl chloride were removed by distillation under reduced pressure and a vicous liquid was obtained. 10 mL of anhydrous chloroform was added to obtain a solution A.

0.958 g (1.18 mmol) of docetaxel was dissolved in 20 mL of chloroform in a 50 mL reaction flask, and 495.9 μL (3.558 mmol) of triethyl amine was added, cooled in an ice-salt bath, and stirred. 10 mL of the solution A was slowly added, and reacted for 4 hrs at room temperature under nitrogen atmosphere. After reaction, chloroform was removed from the reaction solution by distillation under reduced pressure. 20 mL of ethyl acetate was then added to the reaction flask, and stirred. The resulting white solid was filtered off, and then the filtrate was concentrated to 10 mL. After separation by column chromatography with gradient elution (on 100-200 mesh silica gel as a stationary phase, eluting with a mixture of acetonitrile and 1,4-dioxane), 1.205 g of polyethylene glycol monomethyl ether (Mn=1000) docetaxel-2'-diglycolate as a viscous white liquid was obtained (yield 53.6%).

Figure 1:
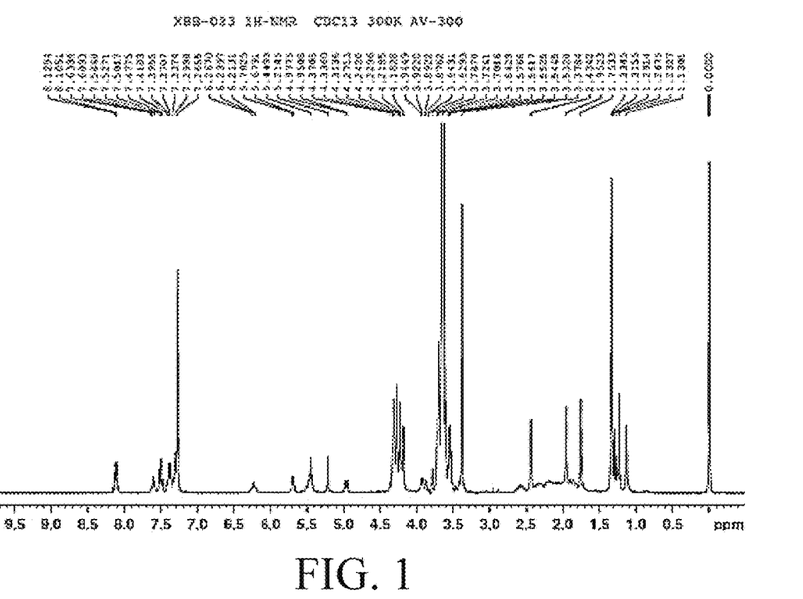
FIG. 1 is a 1H NMR spectrum of a water-soluble docetaxel anticancer drug compound (polyethylene glycol monomethyl ether docetaxel-2'-diglycolate, in which the polyethylene glycol monomethyl ether has an average molecular weight Mn of 1000).
Figure 2:
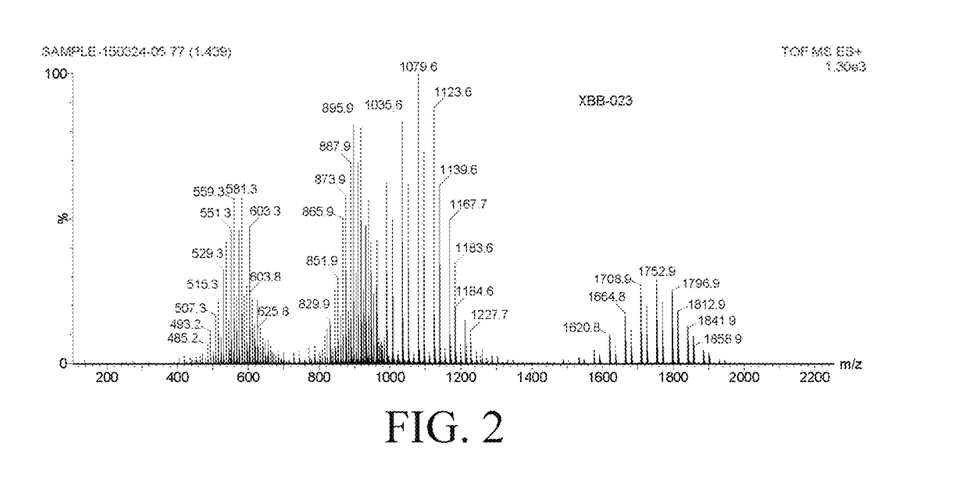
FIG. 2 is a mass spectrum of a water-soluble docetaxel anticancer drug compound (polyethylene glycol monomethyl ether docetaxel-2'-diglycolate, in which the polyethylene glycol monomethyl ether has an average molecular weight Mn of 1000).

The mass spectra and 1H NMR spectrum of the synthesized compound are shown in FIGS. 1 and 2.

MS (Positive ESI): m/z=1885.0, 1840.9, 1796.9, 1752.9, 1708.9, 1664.9, 1620.8, 1576.8.

MS(Negative ESI): m/z=1906, 1861.9, 1816.9, 1773.9, 1728.8, 1685.8, 1640.8, 1596.7, 1553.7, 1508.7.

$^1$H NMR (300 MHz, CDCl3): δ ppm: 8.1294~8.1051 (d, 2H, J=7.29 Hz), 7.6338~7.5848 (t, 1H, J=7.35 Hz), 7.5271~7.4775 (t, 2H, J=7.44 Hz), 7.4258~7.3779 (m, 2H), 7.3465~7.2837 (m, 3H), 6.2670~6.2131 (t, 1H), 5.7025~5.6791 (d, 1H, J=7.02 Hz), 5.4493 (m, 2H), 5.2145 (s, 1H), 4.9775~4.9508 (d, 1H, J=8.01 Hz), 4.3705~4.1828 (m, 9H), 3.9449~3.9220 (d, 1H), 3.6429 (m, 84H), 3.5766~3.5320 (m, 2H), 3.3784 (s, 3H), 2.6156~2.5076 (m, 1H), 2.4342 (s, 3H), 2.4340~2.3501 (m, 2H), 1.9523 (s, 3H), 1.940~1.9109 (m, 1H), 1.9043 (s, 3H), 1.3345 (s, 9H), 1.2327 (s, 3H), 1.1301 (s, 3H).

Example 2. Formulations of Water-Soluble Docetaxel Anticancer Drug Compound (XBB-023)

In this example, injections of XBB-023 with water, saline (0.9% sodium chloride) or a glucose solution (5%) are provided. The injections contain the water-soluble docetaxel anticancer drug compound of the present invention, where the content of each component in the formulation is in percentages by weight.

1). Injection of Water-Soluble Docetaxel Anticancer Drug Compound in Water 100 mg of the water-soluble docetaxel anticancer drug compound (XBB-023) was added to a 10 mL volumetric flask, added with water q.s. to 10 mL, and shaken to provide an injection having a composition comprising:

| XBB-023 | 1.0% |
|---|---|
| Water | 99.0%. |

The injection produced was filtered through a 0.2 μm filter, and filled in a sterilized glass vial.

2) Injection of Water-Soluble Docetaxel Anticancer Drug Compound in Saline (0.9% Sodium Chloride)

50 mg of the water-soluble docetaxel anticancer drug compound (XBB-023) was added to a 10 mL volumetric flask, added with saline (0.9% sodium chloride) q.s. to 10 mL, and shaken to provide an injection having a composition comprising:

| XBB-023 | 0.5% |
|---|---|
| Saline | 99.5%. |

The injection produced was filtered through a 0.2 μm filter, and filled in a sterilized glass vial.

3) Injection of Water-Soluble Docetaxel Anticancer Drug Compound in 5% Glucose Solution 50 mg of the water-soluble docetaxel anticancer drug compound (XBB-023) was added to a 10 mL volumetric flask, added with 5% glucose solution for injection q.s. to 10 mL, and shaken to provide an injection having a composition comprising:

| XBB-023 | 0.5% |
|---|---|
| 5% glucose for injection | 99.5%. |

The injection produced was filtered through a 0.2 μm filter, and filled in a sterilized glass vial.

Example 3. Determination of Micelle Size of Water-Soluble Docetaxel Anticancer Drug Compound (XBB-023)

Micelles were formed after the water-soluble docetaxel anticancer drug compound XBB-023 was dissolved in water. The micelle size was determined by using the ZetaPlus laser scattering particle size analyzer from BROOKHAVEN, USA. 5 mg and 10 mg of the drug (XBB-023) were put into 2 mL of distilled water respectively, stirred to be fully dissolved, and allowed to stand for 10 minutes. After the bubbles disappeared, the liquid was added to a sample cell (cuvette). During the process, caution should be taken to avoid the generation of bubbles. Then, the cuvette was placed in a groove corresponding to the base of the sample cell for measurement. Each sample was triplicated and the three measurements were averaged.

Figure 3:
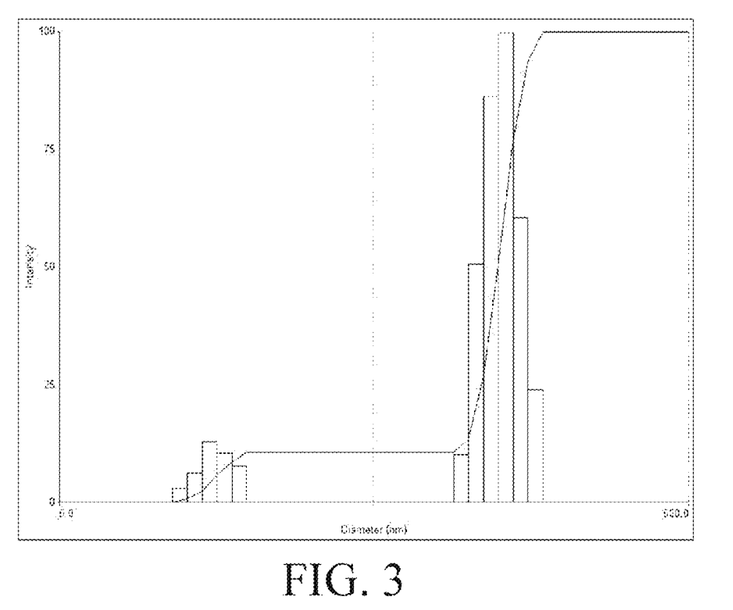
FIG. 3 shows the average micelle size distribution when a solution of the drug compound XBB-023 in water is 2.5 mg/mL.
Figure 4:
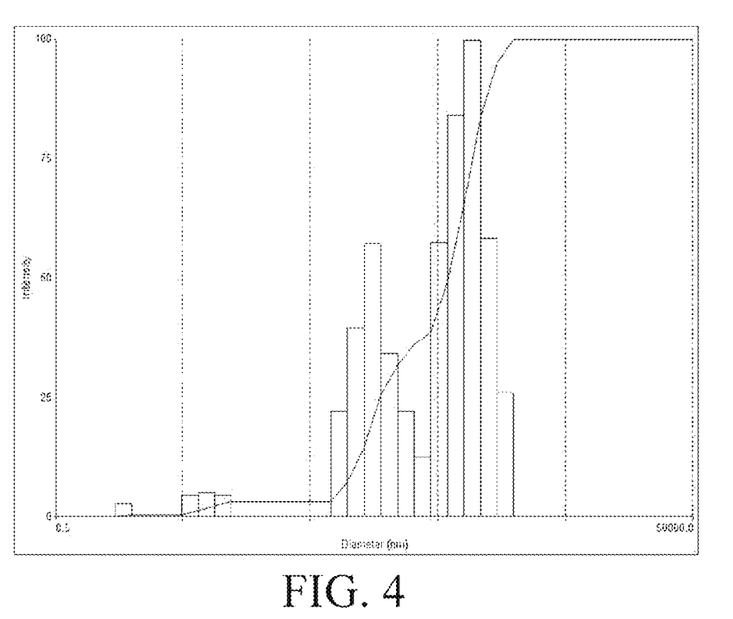
FIG. 4 shows the average micelle size distribution when a solution of the drug compound XBB-023 in water is 5 mg/mL.

The experimental results are shown in FIGS. 3 and 4. The results show that when the concentration of the aqueous XBB-023 solution is 2.5 mg/mL and 5 mg/mL, the average particle size is 101.2 nm and 345.0 nm respectively.

Example 4. In Vitro Test for the Action of Sustained Release of the Water-Soluble Docetaxel Anticancer Drug Compound (XBB-023)

1. Instruments and Reagents

Shimadzu LC-20AT high performance liquid chromatograph, SPD-20A detector, Lab Solutions chromatography workstation (Shimadzu Corporation, Japan); DF-1 heat-collection thermostatic magnetic stirrer (Shanghai Jiangxing Instrument Co., Ltd.); and FA2004B electronic balance (Shanghai Yueping Scientific Instrument Co., Ltd.).

Methanol: chromatographic grade, purchased from Tedia (USA); $KH_2PO_4$ and NaOH: analytically pure, purchased from Sinopharm Chemical Reagent Co., Ltd.; and water for test: distilled water.

A phosphate buffer (0.05M $KH_2PO_4$, 0.04M NaOH) at pH 7.40 was formulated.

2. Test Method 10 mg of XBB-023 was accurately weighed into a screw cultivation flask, and then 3 ml of the phosphate buffer was added, and magnetically stirred until clear.

The oil bath temperature of the heat-collection thermostatic magnetic stirrer was set to 37° C., and the XBB-023 formulation was placed therein for hydrolysis.

At 0, 1, 2, 5, 6, 7, 25, 31, 48, 55, 72, 79, 103, and 168 h after hydrolysis, 60 μL of the XBB-023 reaction solution was pipetted into a chromatographic bottle and 540 μL of acetonitrile was added to obtain a 0.33 mg/ml sample, which was then subjected to HPLC analysis.

3. HPLC Analysis

Chromatographic column: C18 column (5 μm, 150 mm×5 mm); mobile phase: acetonitrile:water (50:50); detection wavelength: 227 nm; flow rate:1.0 ml/min; volume of injection: 5 μL; and column temperature: 40° C.

XBB-023 and docetaxel can be detected simultaneously using the above HPLC analysis conditions. Target retention time $t_{XBB-023}$=9.6 min, and $t_{docetaxel}$=8.0 min.

4. Experimental Results

Figure 5:
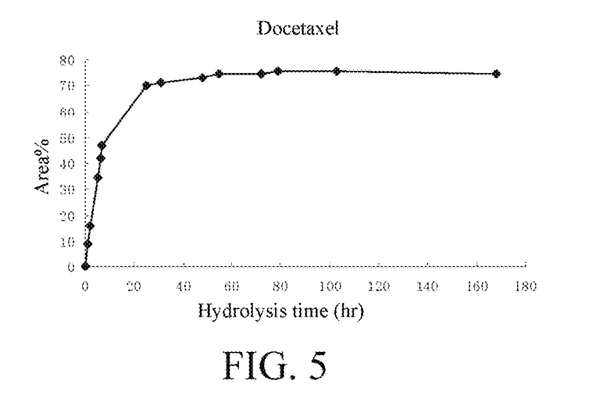
FIG. 5 shows the variation in the content of docetaxel in percent by weight at various times after the hydrolysis of the drug compound XBB-023.
Figure 6:
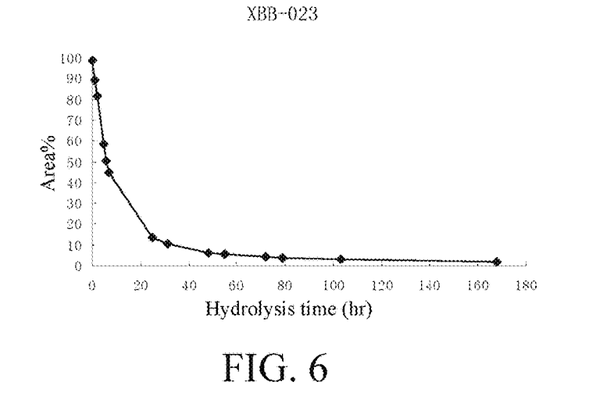
FIG. 6 shows the variation in the content of the drug compound XBB-023 in percent by weight at various times after the hydrolysis.
Figure 7:
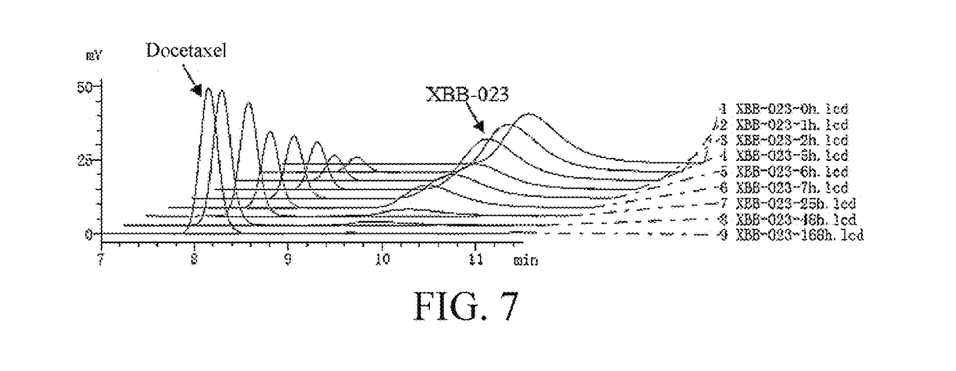
FIG. 7 shows three dimensional overlay chromatograms of the drug compound XBB-023 after hydrolysis.
Figure 8:
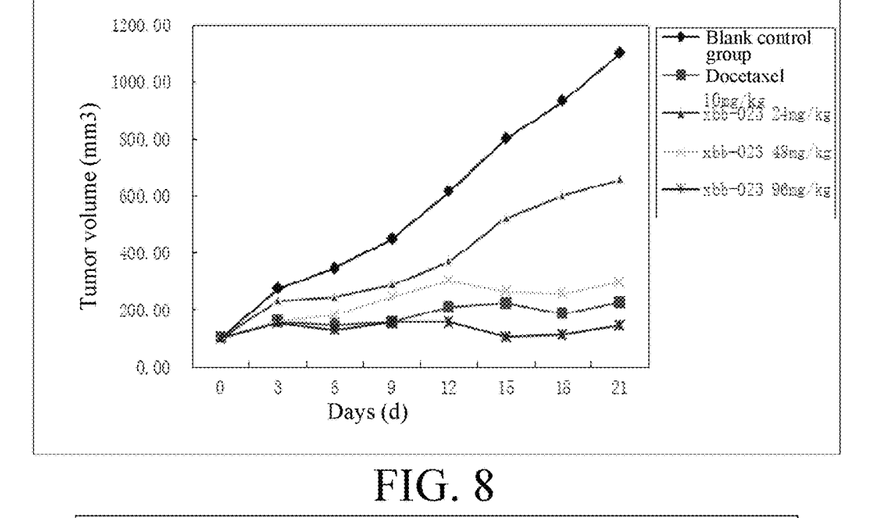
FIG. 8 shows the growth inhibition of the drug compound XBB-023 on A549 human lung cancer xenografts in nude mice.
Figure 9:
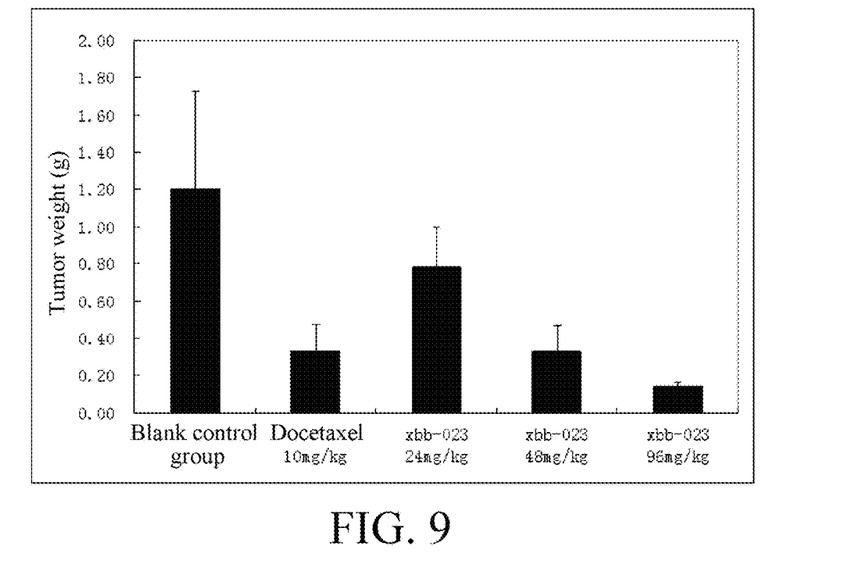
FIG. 9 shows the effect of the drug compound XBB-023 on the tumor weight of A549 human lung cancer xenografts in nude mice.

The percentage contents of docetaxel and XBB-023 at various times after the hydrolysis of XBB-023 can be obtained by area normalization method. The experimental results are shown in Tables 1 and 2, and FIGS. 5, 6 and 7. It can be known from the comparison of the chromatograms of XBB-023 at various hydrolysis times that with the elapse of time, the XBB-023 peak area gradually declines and the peak height gradually decreases. In the meanwhile, a peak appears at the retention time of docetaxel, the peak area gradually increases, and the peak height rises gradually. This suggests that XBB-023 is continuously hydrolyzed to release docetaxel over the time.

TABLE 1

Percentage content of docetaxel at various times after the hydrolysis of XBB-023

| Hydrolysis time (hr) | Area % |
|---|---|
| 0 | 0.151 |
| 1 | 8.764 |
| 2 | 15.654 |

TABLE 1-continued

Percentage content of docetaxel at various times after the hydrolysis of XBB-023

| Hydrolysis time (hr) | Area % |
|---|---|
| 5 | 34.732 |
| 6 | 41.899 |
| 7 | 46.871 |
| 25 | 70.097 |
| 31 | 70.969 |
| 48 | 73.189 |
| 55 | 74.509 |
| 72 | 74.38 |
| 79 | 75.506 |
| 103 | 75.61 |
| 168 | 74.708 |

TABLE 2

Percentage content of XBB-023 at various times after the hydrolysis of XBB-023

| Hydrolysis time (hr) | Area % |
|---|---|
| 0 | 98.489 |
| 1 | 89.088 |
| 2 | 81.724 |
| 5 | 58.427 |
| 6 | 50.359 |
| 7 | 44.823 |
| 25 | 13.289 |
| 31 | 10.279 |
| 48 | 6.213 |
| 55 | 5.384 |
| 72 | 4.156 |
| 79 | 3.861 |
| 103 | 3.299 |
| 168 | 1.721 |

5. Conclusions

The results show that the drug compound XBB-023 can be gradually hydrolyzed to release docetaxel in vitro in a buffer solution (pH 7.40) at 37° C. Therefore, as a prodrug, the drug compound XBB-023 can be directly dissolved in water, saline, or a glucose solution to prepare an injection or other preparations, which can release docetaxel in vivo to inhibit the tumor growth.

Example 5. Pharmacodynamic Test of Growth Inhibition of Water-Soluble Docetaxel (XBB-023) on A549 Human Lung Cancer Xenografts in Nude Mice 1) Formulation Method 48 mg of the drug XBB-023 was accurately weighed at each administration, to which 10 ml of 0.9% sodium chloride solution (manufactured by Chenxin Pharmaceutical Co., Ltd.; lot number: 1403222705; specification: 250 ml: 12.5 g) was added to give a concentration of 4.8 mg/ml. The dose volume was 0.4 ml per 20 g, that is, the dose was 96 mg/kg. Then, the solution was diluted to other desired concentrations with 0.9% sodium chloride solution.

2) Control Agent

Docetaxel injection, manufactured by Jiangsu Hengrui Pharmaceutical Co., Ltd., lot number: 15011215, specification: 0.5 ml: 20 mg. Formulation method: during use, 20 mg of docetaxel injection of the above specification was added to 1.5 ml of a solvent for the docetaxel injection to give a concentration of 10 mg/ml, and then fully diluted with saline to 1 mg/ml. The dose volume was 0.2 ml per 20 g, that is, the dose was 10 mg/kg.

3) Source, Germline, and Strain of Test Animals

BALB/c nude mice, provided by Changzhou Kavens Laboratory Animal Co., Ltd. (Experimental Animal Production License: SOCK (Su) 2011-0003), age: 35-40 days, weight: 18-24 g, female.

4) Grouping of Test Animals

| | |
|---|---|
| Negative control group (Blank control) | 12 animals |
| Positive control group (Docetaxel, 10 mg/kg) | 6 animals |
| Treatment group (XBB-023, 96 mg/kg) | 6 animals |
| Treatment group (XBB-023, 48 mg/kg) | 6 animals |
| Treatment group (XBB-023, 24 mg/kg) | 6 animals |

5) Xenografts

A549 human lung cancer xenografts in nude mice was established by inoculating human lung cancer A549 cell line subcutaneously to the axillary fossa of nude mice in an amount of $2*10^6$ cells/animal.

6) Test Method

Human lung cancer A549 cell line in logarithmic growth phase was prepared into a cell suspension of $1\times10^8$ cells/ml under aseptic conditions and subcutaneously inoculated to the right axillary fossa of nude mice in a volume of 0.1 ml. The size of the xenograft in the nude mice was measured with a vernier caliper. After the xenografts grew to 100-300 mm$^3$, the animals were randomly grouped. The anti-tumor effect of the test agents was dynamically observed by measuring the size of the xenografts. The size of the xenografts was measured once every 3 days. The dose volume was 0.4 ml/20 g. Twenty-one days later, the mice were sacrificed and the tumors were surgically excised and weighed. The tumor volume (TV) is calculated by a formula below:

$$TV = \tfrac{1}{2} \times a \times b^2$$

in which a and b denote the length and width respectively.

The relative tumor volume (RTV) is calculated based on the measurements by a formula: $RTV = V_t/V_0$, where $V_0$ is the measured tumor volume upon being caged (i.e., $d_0$) and $V_t$ is the tumor volume at each measurement. The evaluation index of the anti-tumor activity is relative tumor growth rate T/C (%), which is calculated by a formula below:

$$T/C\ (\%) = \frac{T_{RTV}}{C_{RTV}} \times 100$$

in which $T_{RTV}$ is the RTV of the treatment group; and $C_{RTV}$ is the RTV of the negative control group.

The tumor inhibition rate is calculated by a formula below:

$$\text{Tumor inhibition rate } (\%) = \left(1 - \frac{T_{weight}}{C_{weight}}\right) \times 100$$

$T_{weight}$ is the average tumor weight of the treatment group; and $C_{weight}$ is the average tumor weight of the negative control group.

7) Results and Discussion

The experimental results are shown in Tables 3 and 4, and FIGS. 8 to 11. The drug XBB-023 is administered via the tail vein at the doses of 96 mg/kg, 48 mg/kg, and 24 mg/kg, respectively, once every 3 days for a total of 7 doses. The T/C ratio of the A549 human lung cancer xenografts in nude mice in the experimental groups is 12.83%, 25.56%, and 56.30%, respectively; and the tumor inhibition rate is 88.45%, 68.55%, and 34.73%. After docetaxel (10 mg/kg) is administered once every 3 days via tail vein injection for a total of 7 doses, the T/C ratio of the A549 human lung cancer xenografts in nude mice is 21.15% and the tumor inhibition rate is 72.16%.

Figure 10:
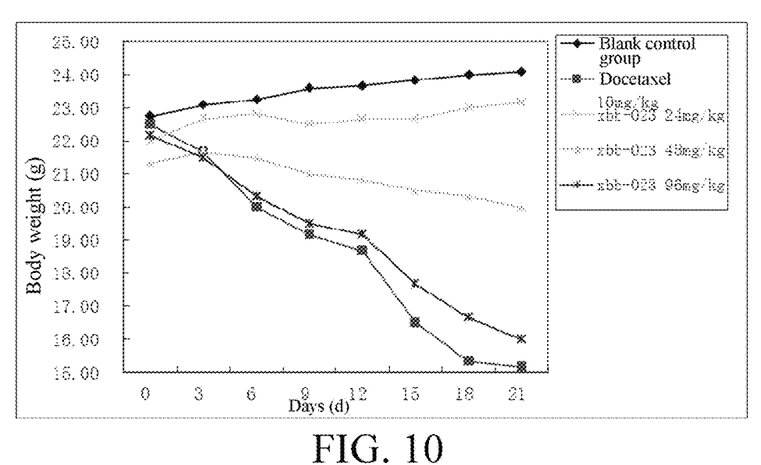
FIG. 10 shows the effect of the drug compound XBB-023 on the body weight of the test animals, that is, nude mice with A549 human lung cancer xenografts.
Figure 11:
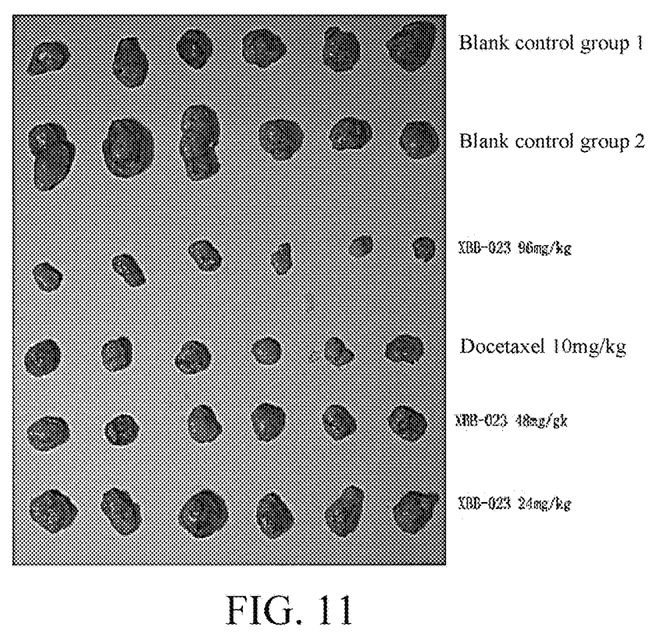
FIG. 11 shows photographs showing the growth inhibition of the drug compound XBB-023 on nude mice with A549 human lung cancer xenografts.

Extremely significant effect on the body weight of the experimental mice (P<0.01) is exhibited in the positive control group administered with 10 mg/kg docetaxel and in the group administered with 96 mg/kg XBB-023, and significant effect on the body weight of the experimental mice (P<0.05) is exhibited in the group administered with 48 mg/kg XBB-023. The test results show that the inhibition rate of the drug XBB-023 at 96 mg/kg is 16.29% higher than that in the positive control group with 10 mg/kg docetaxel, but the effect on the body weight of the experimental mice is less, indicating that the efficacy of XBB-023 at a high dose is better than that of docetaxel, and the toxicity is lower.

TABLE 3

Effect of the drug XBB-023 on the tumor volume of A549 human lung cancer xenografts in nude mice (X ± SD, Tumor volume: in mm$^3$)

| Group | Dosage (mg/kg) | 0 d Tumor volume | 3 d Tumor volume | 3 d RTV | 3 d T/C | 6 d Tumor volume | 6 d RTV | 6 d T/C |
|---|---|---|---|---|---|---|---|---|
| Blank control group | — | 100.53 ± 20.71 | 275.54 ± 90.21 | 2.88 ± 1.17 | — | 348.56 ± 80.33 | 3.60 ± 1.04 | — |
| Docetaxel | 10 | 100.58 ± 20.87 | 157.30 ± 26.48** | 1.62 ± 0.37** | 56.09% | 147.47 ± 41.99** | 1.49 ± 0.39** | 41.39% |
| XBB-023 | 96 | 102.83 ± 14.74 | 154.44 ± 15.73** | 1.54 ± 0.31** | 53.47% | 129.15 ± 19.29** | 1.26 ± 0.15** | 35.11% |
| XBB-023 | 48 | 101.49 ± 18.47 | 159.57 ± 38.77** | 1.59 ± 0.35** | 55.23% | 180.89 ± 31.39** | 1.80 ± 0.18** | 49.90% |
| XBB-023 | 24 | 101.08 ± 20.73 | 232.16 ± 79.30* | 2.27 ± 0.52** | 78.90% | 244.45 ± 80.88** | 2.38 ± 0.37** | 66.13% |

TABLE 3-continued

Effect of the drug XBB-023 on the tumor volume of A549 human lung cancer
xenografts in nude mice (X ± SD, Tumor volume: in mm³)

| | | | 9 d | | | 12 d | | |
|---|---|---|---|---|---|---|---|---|
| | | | Tumor volume | RTV | T/C | Tumor volume | RTV | T/C |
| Blank control group | — | 100.53 ± 20.71 | 449.69 ± 83.72 | 4.65 ± 1.17 | — | 617.35 ± 78.42 | 6.37 ± 133 | — |
| Docetaxel | 10 | 100.58 ± 20.87 | 155.55 ± 44.12** | 1.59 ± 0.47** | 34.23% | 208.93 ± 68.26** | 2.15 ± 0.81** | 33.77% |
| XBB-023 | 96 | 102.83 ± 14.74 | 15628 ± 17.71** | 1.54 ± 0.22** | 33.18% | 156.91 ± 35.05** | 1.54 ± 0.33** | 24.19% |
| XBB-023 | 48 | 1.01.49 ± 18.47 | 245.14 ± 40.82** | 2.46d ± 0.37** | 52.80% | 302.66 ± 60.48 | 3.02 ± 0.53 | 47.50% |
| XBB-023 | 24 | 101.08 ± 20.73 | 289.34 ± 82.35** | 2.85 ± 0.39** | 61.19% | 371.41 ± 95.01** | 3.68 ± 0.51** | 57.80% |

| | | | 15 d | | | 18 d | | |
|---|---|---|---|---|---|---|---|---|
| | | | Tumor volume | RTV | T/C | Tumor volume | RTV | T/C |
| Blank control group | — | 100.53 ± 20.71 | 802.08 ± 171.71 | 8.36 ± 2.57 | — | 932.09 ± 302.48 | 9.69 ± 3.70 | — |
| Docetaxel | 10 | 100.58 ± 20.87 | 224.22 ± 57.63** | 2.24 ± 0.43** | 26.80% | 186.80 ± 42.03** | 1.87 ± 0.28** | 19.30% |
| XBB-023 | 96 | 102.83 ± 14.74 | 107.31 ± 27.45** | 1.06 ± 0.28** | 12.63% | 114.16 ± 17.61** | 1.13 ± 0.21** | 11.66% |
| XBB-023 | 48 | 101.49 ± 18.47 | 264.78 ± 68.29** | 2.61 ± 0.47** | 31.23% | 257.22 ± 76.37** | 2.50 ± 0.37** | 25.76% |
| XBB-023 | 24 | 101.08 ± 20.73 | 522.84 ± 249.70* | 4.91 ± 1.58** | 58.72% | 602.28 ± 288.50** | 5.68 ± 1.66** | 58.60% |

| | | | 21 d | | |
|---|---|---|---|---|---|
| | | | Tumor volume | RTV | T/C |
| Blank control group | — | 100.53 ± 20.71 | 1103.90 ± 314.12 | 11.34 ± 3.41 | — |
| Docetaxel | 10 | 100.58 ± 20.87 | 226.65 ± 56.45* | 2.40 ± 0.99* | 21.15% |
| XBB-023 | 96 | 102.83 ± 14.74 | 146.15 ± 20.51** | 1.46 ± 0.32** | 12.83% |
| XBB-023 | 48 | 101.49 ± 18.47 | 299.13 ± 86.76** | 2.90 ± 0.37** | 25.56% |
| XBB-023 | 24 | 101.08 ± 20.73 | 660.00 ± 210.71* | 6.39 ± 0.81* | 56.30% |

Note:
compared with the blank control group, *P < 0.05, **P < 0.01

TABLE 4

Inhibition of the drug XBB-023 on the tumor growth of A549 human lung cancer
xenografts in nude mice (X ± SD)

| Group | Dosage (mg/kg) | Administration frequency | Initial body weight (g) | Initial number of animals | Final body weight (g) | Final number of animals | Tumor weight (g) | Tumor inhibition rate (%) |
|---|---|---|---|---|---|---|---|---|
| Blank control group | — | — | 22.75 ± 1.92 | 12 | 24.08 ± 2.06 | 12 | 1.20 ± 0.53 | — |
| Docetaxel | 10 | Once every 3 days | 22.50 ± 1.26 | 6 | 15.17 ± 0.90** | 6 | 0.33 ± 0.15** | 72.16% |
| XBB-023 | 96 | Once every 3 days | 22.00 ± 0.82 | 6 | 16.00 ± 2.31** | 6 | 0.14 ± 0.03** | 88.45% |
| XBB-023 | 48 | Once every 3 days | 21.33 ± 1.37 | 6 | 20.00 ± 0.82** | 6 | 0.38 ± 0.14** | 68.55% |
| XBB-023 | 24 | Once every 3 days | 22.17 ± 1.57 | 6 | 23.17 ± 0.90* | 6 | 0.78 ± 0.22 | 34.73% |

Compared with the blank control group, *P < 0.05, **P < 0.01

The invention claimed is:

1. A water-soluble docetaxel anticancer drug compound of Formula I below:

I wherein R is C1-C5 alkyl, and n=5-500.

2. The water-soluble docetaxel anticancer drug compound according to claim 1, wherein in Formula I, R=—CH$_3$, —CH$_2$CH$_3$, —CH$_2$CH$_2$CH$_3$, or —CH$_2$CH$_2$CH$_2$CH$_3$.

3. A method for preparing the water-soluble docetaxel anticancer drug compound according to claim 1, comprising:
 1) reacting a polyethylene glycol monoalkyl ether with diglycolic acid or diglycolic anhydride to produce a polyethylene glycol monoalkyl ether diglycolate; and
 2) reacting the polyethylene glycol monoalkyl ether diglycolate obtained from Step (1), or an acyl chlorinated product of the polyethylene glycol monoalkyl ether diglycolate with docetaxel to produce the water-soluble docetaxel anticancer drug compound of Formula I.

4. The method according to claim 3, wherein, in Step (1), the reaction between the polyethylene glycol monoalkyl ether with diglycolic anhydride is carried out in the presence of tin (II) 2-ethylhexanoate, aluminum trichloride, or cesium carbonate as a catalyst.

5. An injection of the water-soluble docetaxel anticancer drug compound according to claim 1, comprising
 the water-soluble docetaxel anticancer drug compound of Formula I and one liquid that is water, saline, or a glucose solution.

6. The injection according to claim 5, wherein the drug compound of Formula I accounts for 0.005% to 5.0% by weight of a total weight of the injection.

7. The method according to claim 3, wherein, in Step (1), the reaction between the polyethylene glycol monoalkyl ether with diglycolic acid is carried out in the presence of 4-dimethylaminopyridine and 2-chloro-1-methylpyridinium iodide as a catalyst, or in the presence of N,N'-dicyclohexylcarbodiimide and 4-dimethylaminopyridine as a catalyst.

8. The method according to claim 3, wherein, in Step (2), the acyl chlorinated product of the polyethylene glycol monoalkyl ether diglycolate is obtained by reacting the polyethylene glycol monoalkyl ether diglycolate with an acyl chlorinating agent.

9. The method according to claim 8, wherein the reaction between the acyl chlorinated product of the polyethylene glycol monoalkyl ether diglycolate with docetaxel is in the presence of a base as a catalyst to produce the water-soluble docetaxel anticancer drug compound of Formula I.

10. The method according to claim 3, wherein the reaction between the polyethylene glycol monoalkyl ether diglycolate with docetaxel is carried out in the presence of 4-dimethylaminopyridine and 2-chloro-1-methylpyridinium iodide as a catalyst or in the presence of N,N'-dicyclohexylcarbodiimide and 4-dimethylaminopyridine as a catalyst.

11. The method according to claim 8, wherein the acyl chlorinating agent is thionyl chloride.

12. The method according to claim 9, wherein the base is selected from the group consisting of triethyl amine, pyridine, 4-dimethylaminopyridine, sodium carbonate, potassium carbonate, and cesium carbonate.

13. A method of treating cancer, comprising: administering the water-soluble docetaxel anticancer drug compound of Formula I according to claim 1 to a patient in need thereof, wherein the cancer is human lung cancer.

* * * * *